(12) United States Patent
Kimura et al.

(10) Patent No.: US 11,774,378 B2
(45) Date of Patent: Oct. 3, 2023

(54) FOREIGN SUBSTANCE INSPECTION METHOD AND FOREIGN SUBSTANCE INSPECTION APPARATUS

(71) Applicant: TOYOTA JIDOSHA KABUSHIKI KAISHA, Toyota (JP)

(72) Inventors: Miki Kimura, Nagoya (JP); Tatsuyuki Asada, Nagoya (JP); Yoshiki Koike, Gifu (JP)

(73) Assignee: TOYOTA JIDOSHA KABUSHIKI KAISHA, Toyota (JP)

(*) Notice: Subject to any disclaimer, the term of this patent is extended or adjusted under 35 U.S.C. 154(b) by 625 days.

(21) Appl. No.: 17/022,462

(22) Filed: Sep. 16, 2020

(65) Prior Publication Data

US 2021/0190706 A1 Jun. 24, 2021

(30) Foreign Application Priority Data

Dec. 24, 2019 (JP) ................................ 2019-232507

(51) Int. Cl.
*G01N 23/18* (2018.01)
*G01N 33/44* (2006.01)
(Continued)

(52) U.S. Cl.
CPC ........... *G01N 23/18* (2013.01); *B29C 45/768* (2013.01); *G01N 21/94* (2013.01); *G01N 21/952* (2013.01); *G01N 23/04* (2013.01); *G01N 23/083* (2013.01); *G01N 33/442* (2013.01); *G06T 7/0004* (2013.01); *B29C 2945/76147* (2013.01); *G01N 2223/646* (2013.01); *G06T 2207/30108* (2013.01); *Y02T 90/40* (2013.01)

(58) Field of Classification Search
CPC ...... G01N 23/18; G01N 21/94; G01N 21/952; G01N 33/442
See application file for complete search history.

(56) References Cited

U.S. PATENT DOCUMENTS

2006/0066846 A1* 3/2006 Chen ................... G01N 21/896
356/239.1
2021/0181125 A1* 6/2021 Watanabe .............. G01N 23/04
2022/0057342 A1* 2/2022 Sugihara ................ G01B 15/00

FOREIGN PATENT DOCUMENTS

JP 11037956 A * 2/1999
JP 11326225 A * 11/1999
(Continued)

*Primary Examiner* — Ryan D Walsh
(74) *Attorney, Agent, or Firm* — Sughrue Mion, PLLC (57) ABSTRACT

Provided is a foreign substance inspection method for inspecting presence or absence of a foreign substance embedded in a tubular resin molded product. A dome is prepared. The foreign substance inspection method includes: a first measurement step of measuring a dimension of a first projection image of the embedded foreign substance; a second measurement step of measuring a dimension of a second projection image of the embedded foreign substance: and a calculation step of calculating the dimension of the embedded foreign substance based on a proportional relationship between the dimension of each of the projection images to a distance from a corresponding one of the light sources to the each of the projection images and the dimension of the embedded foreign substance to a distance from the corresponding one of the light sources to the embedded foreign substance.

5 Claims, 4 Drawing Sheets

(51) Int. Cl.
*G01N 21/94* (2006.01)
*G01N 21/952* (2006.01)
*B29C 45/76* (2006.01)
*G01N 23/083* (2018.01)
*G01N 23/04* (2018.01)
*G06T 7/00* (2017.01)

(56) References Cited

FOREIGN PATENT DOCUMENTS

| | | | | |
|---|---|---|---|---|
| JP | 6508435 | B1 | 5/2019 | |
| KR | 20170029954 | A * | 3/2017 | |
| WO | 2017/187818 | A1 | 11/2017 | |
| WO | WO-2020004435 | A1 * | 1/2020 | ........... B07C 5/3416 |

* cited by examiner

FOREIGN SUBSTANCE INSPECTION METHOD AND FOREIGN SUBSTANCE INSPECTION APPARATUS

CROSS-REFERENCE TO RELATED APPLICATION

This application claims priority to Japanese Patent Application No. 2019-232507 filed on Dec. 24, 2019, incorporated herein by reference in its entirety.

BACKGROUND

1. Technical Field

The present disclosure relates to a foreign substance inspection method and a foreign substance inspection apparatus each for inspecting the presence or absence of a foreign substance embedded in a tubular resin molded product and having a dimension larger than a predetermined threshold.

2. Description of Related Art

There has been conventionally known a fuel cell vehicle including a fuel cell configured to generate electric power by chemically reacting hydrogen taken in from a hydrogen tank provided in a vehicle with oxygen taken in from the atmosphere, and the fuel cell vehicle travels by use of the electric power generated by the fuel cell as a drive source. From the viewpoint of weight reduction, as the hydrogen tank provided in the fuel cell vehicle, it is general to use a high-pressure tank configured such that a sealed cylindrical liner constituted by a pipe and domes made of resin is provided as an inner shell, and a high-strength outer shell is formed by winding carbon fiber around the outer peripheral surface of the liner.

In the meantime, the liner constituting the inner shell of the hydrogen tank serves as a container in which high-pressure hydrogen gas is filled in an airtight manner, and therefore, the liner is required to have a gas barrier property to low-molecular gas. On this account, as a molding material for the pipe and the domes as component parts of the liner, it is major to use a nylon material having a high gas barrier property. Further, in consideration of productivity, it is general to mold the cylindrical pipe and the bottomed tubular domes by injection molding.

However, the pipe and the domes molded by injection molding by use of the nylon material have such problems that nylon is a material that easily deteriorates and degrades due to a heat history, and it is difficult to cause the material not to remain and stay at all in an injection path. In combination of these problems, a foreign substance (hereinafter also referred to as an "embedded foreign substance") mainly made of a carbonized deteriorated substance and called a "black spot" may be included in the pipe and the domes.

In a case where a relatively large amount of embedded foreign substances or a relatively large embedded foreign substance is included in a product (the pipe and the domes), the mechanical strength of the liner decreases as a result. Accordingly, it is important to check the "amount" and "magnitude" of the embedded foreign substance included in the product. In this respect, the amount and magnitude of the embedded foreign substance present on a surface of the product are easily checkable by visual observation. Generally, in order to prevent weatherability deterioration due to ultraviolet rays, the nylon material as the molding material for the liner includes color pigment, in other words, the product is not transparent. Accordingly, it may be said that it is difficult to check the presence or absence of the embedded foreign substance present inside the product, and further, it is difficult to check the magnitude of the embedded foreign substance by visual observation.

In view of this, for example, Japanese Patent No. 6508435 (JP 6508435 B) describes the following inspection method for inspecting a resin molded product. That is, X-rays are emitted in a plurality of paths, and the X-rays that have passed through the resin molded product are detected at one or more positions. Then, a defect-suspected part (a gap or impurity) is detected from a detected X-ray image, and the height of the defect-suspected part is measured by a stereo matching method. After that, a logical product of an obtained height information image and an image obtained as the defect-suspected part is taken, so that the quality of the defect-suspected part is sorted based on the height position.

SUMMARY

However, the technique to detect an embedded foreign substance by use of X-rays like the technique of JP 6508435 B is unrealistic from the viewpoint of an increase in cost due to introduction of an X-radiation facility or the like, safety management of X-rays (radioactive rays), and so on.

On this account, currently, in a case where the presence of an embedded foreign substance inside products is slightly recognized by visual observation, the products are all handled as defective products without checking the magnitude of the embedded foreign substance. This decreases the yield of the liner and causes an increase in cost.

The present disclosure is accomplished in view of such a problem, and an object of the present disclosure is to provide a technology to calculate, with high accuracy, the dimension of a foreign substance embedded in a tubular resin molded product by a safe and simple technique.

In order to achieve the above object, a foreign substance inspection method according to the present disclosure is to calculate the dimension of an embedded foreign substance based on a projection image of the embedded foreign substance by light emitted from a light source, by use of such a property that nylon that does not include color pigment allows light to pass therethrough.

More specifically, the present disclosure is aimed at a foreign substance inspection method for inspecting the presence or absence of a foreign substance embedded in a tubular resin molded product and having a dimension larger than a predetermined threshold.

In the foreign substance inspection method, a resin molded product made of nylon that does not include color pigment is prepared as the resin molded product.

The foreign substance inspection method includes: a first measurement step of emitting light to a first peripheral surface of the resin molded product from a first light source and measuring a dimension of a first projection image, of an embedded foreign substance, that is projected on a second peripheral surface, the first light source being placed on either one of inside and outside of the resin molded product in the tubular radial direction; a second measurement step of emitting light to the second peripheral surface of the resin molded product from a second light source and measuring a dimension of a second projection image, of the embedded foreign substance, that is projected on the first peripheral surface, the second light source being placed on the other one of the inside and the outside of the resin molded product in the tubular radial direction; and a calculation step of calculating a dimension of the embedded foreign substance based on a proportional relationship between a dimension of each of the projection images projected by the light sources to a distance from a corresponding one of the light sources to the each of the projection images and a dimension of the embedded foreign substance to a distance from the corresponding one of the light sources to the embedded foreign substance.

In this configuration, the resin molded product made of nylon that does not include color pigment is used as an inspection target. Accordingly, when light is emitted to the inner peripheral surface of the resin molded product from the light source placed inside the resin molded product, for example, the light passes through the resin molded product, so that a projection image of the embedded foreign substance is projected on the outer peripheral surface of the resin molded product. Hereby, the dimension of the projection image of the embedded foreign substance can be measured. Similarly, when light is emitted to the outer peripheral surface of the resin molded product from the light source placed outside the resin molded product, a projection image of the embedded foreign substance is projected on the inner peripheral surface of the resin molded product, so that the dimension of the projection image of the embedded foreign substance can be measured.

Further, there is a proportional relationship between the dimension of the first projection image to the distance from the first light source to the first projection image and the dimension of the embedded foreign substance to the distance from the first light source to the embedded foreign substance, and there is also a similar proportional relationship between the dimension of the second projection image to the distance from the second light source to the second projection image and the dimension of the embedded foreign substance to the distance from the second light source to the embedded foreign substance. In other words, two equations (proportional relationships) are established for two unknown quantities, i.e., the "distance from the light source to the embedded foreign substance" and the "dimension of the embedded foreign substance." Accordingly, the dimension of the embedded foreign substance can be calculated based on these proportional relationships.

Thus, with the present disclosure, it is possible to calculate the dimension of the embedded foreign substance with high accuracy by a safe and simple technique to emit light from the inner and outer light sources in the tubular radial direction to the resin molded product made of nylon that does not include color pigment.

Further, the calculation step may include: a first calculation step of calculating a distance from either one of the first and second light sources to the embedded foreign substance by use of an embedment depth of the embedded foreign substance, the embedment depth being calculated based on a proportional relationship between the dimension of the first projection image to a distance from the first light source to the first projection image and the dimension of the embedded foreign substance to a distance from the first light source to the embedded foreign substance, and a proportional relationship between the dimension of the second projection image to a distance from the second light source to the second projection image and the dimension of the embedded foreign substance to a distance from the second light source to the embedded foreign substance; and a second calculation step of calculating the dimension of the embedded foreign substance based on a proportional relationship between the dimension of a projection image projected by the one of the first and second light sources to the distance from the one of the first and second light sources to the projection image and the dimension of the embedded foreign substance to the distance from the one of the first and second light sources to the embedded foreign substance.

In this configuration, first, the embedment depth of the embedded foreign substance is calculated based on the two equations (proportional relationships), and then, by use of the embedment depth thus calculated, the "distance from the light source to the embedded foreign substance" as one of the unknown quantities is calculated. After that, the "distance from the light source to the embedded foreign substance" is substituted into either of the two equations, so that the "dimension of the embedded foreign substance" as the other one of the unknown quantities can be easily calculated.

In the meantime, the dimension of the projection image, of the embedded foreign substance, that is projected on the outer peripheral surface of the resin molded product by the light from the light source placed inside the resin molded product can be measured by an inspector by visual observation regardless of the size of the diameter of the tubular resin molded product. On the other hand, the dimension of the projection image, of the embedded foreign substance, that is projected on the inner peripheral surface of the resin molded product by the light from the light source placed outside the resin molded product might be difficult to be measured by the inspector by visual observation depending on the size of the diameter of the tubular resin molded product. On this account, in a case where the diameter of the resin molded product is relatively small, it is conceivable that an image of at least the projection image, of the embedded foreign substance, that is projected on the inner peripheral surface of the resin molded product is captured by a camera placeable inside the resin molded product, and the dimension of the projection image is measured based on the image thus captured.

However, in a case where the dimension of one of the projection images is directly measured by visual observation, and the dimension of the other one of the projection images is measured via a captured image, a slight measurement error might be caused between them.

In view of this, in the foreign substance inspection method, in the first and second measurement steps, images of the first and second projection images may be captured by respective cameras, and respective dimensions of the first and second projection images may be measured based on the images thus captured.

With this configuration, in a case where an image of the projection image, of the embedded foreign substance, that is projected on the inner peripheral surface of the resin molded product is captured by the camera, an image of the projection image, of the embedded foreign substance, that is projected on the outer peripheral surface of the resin molded product is also captured by the camera, and the dimension of the projection image is measured based on the image thus captured. Accordingly, respective dimensions of the projection images, of the embedded foreign substance, that are projected on the inner peripheral surface and the outer peripheral surface of the resin molded product, respectively, can be measured while the measurement error is restrained.

Further, the present disclosure is also aimed at a foreign substance inspection apparatus used for the foreign substance inspection method.

The foreign substance inspection apparatus includes an inner light source, an outer light source, a support base, a camera, a displaying unit, and a measuring unit. The inner light source is placed inside the resin molded product in the tubular radial direction such that the inner light source is movable in the tubular axial direction. The outer light source is placed outside the resin molded product in the tubular radial direction such that the outer light source is movable in the tubular axial direction. The support base is configured to support the resin molded product such that the resin molded product is rotatable in a circumferential direction. The camera is placed at least inside the resin molded product in the tubular radial direction such that the camera is movable in the tubular axial direction, the camera being configured to take an image of an inner peripheral surface of the resin molded product. The displaying unit is configured to display the image captured by the camera on a screen. The measuring unit is configured to measure a dimension of a projection image of the embedded foreign substance when an inspector specifies, on the screen, a border of the projection image, of the embedded foreign substance, that is displayed on the displaying unit.

In this configuration, two light sources are placed inside and outside the resin molded product in the tubular radial direction such that the light sources are movable in the tubular axial direction, and the resin molded product is supported by the support base such that the rein molded product is rotatable in the circumferential direction. Accordingly, it is possible to inspect the presence or absence of the embedded foreign substance over the whole length and the whole circumference of the tubular resin molded product. Besides, by such a simple operation that the inspector specifies, on the screen, a border of the projection image, of the embedded foreign substance, that is displayed on the displaying unit, the dimension of the projection image of the embedded foreign substance can be measured.

Thus, with the present disclosure, it is possible to calculate, with high accuracy, the dimension of the embedded foreign substance over the whole length and the whole circumference of the tubular resin molded product by a safe and simple technique.

Further, the foreign substance inspection apparatus may further include a camera placed outside the resin molded product in the tubular radial direction such that the camera is movable in the tubular axial direction, the camera being configured to capture an image of the outer peripheral surface of the resin molded product.

With this configuration, respective dimensions of the projection images, of the embedded foreign substance, that are projected on the inner peripheral surface and the outer peripheral surface of the resin molded product, respectively, can be measured by the same measurement technique, so that a measurement error can be restrained.

As described above, with the foreign substance inspection method and the foreign substance inspection apparatus according to the present disclosure, it is possible to calculate, with high accuracy, the dimension of the foreign substance embedded in the tubular resin molded product by a safe and simple technique.

BRIEF DESCRIPTION OF THE DRAWINGS

Features, advantages, and technical and industrial significance of exemplary embodiments of the disclosure will be described below with reference to the accompanying drawings, in which like signs denote like elements, and wherein.

DETAILED DESCRIPTION OF EMBODIMENTS

With reference to the drawings, the following describes an embodiment to carry out the present disclosure.

Embodiment 1

Liner

Figure 1:
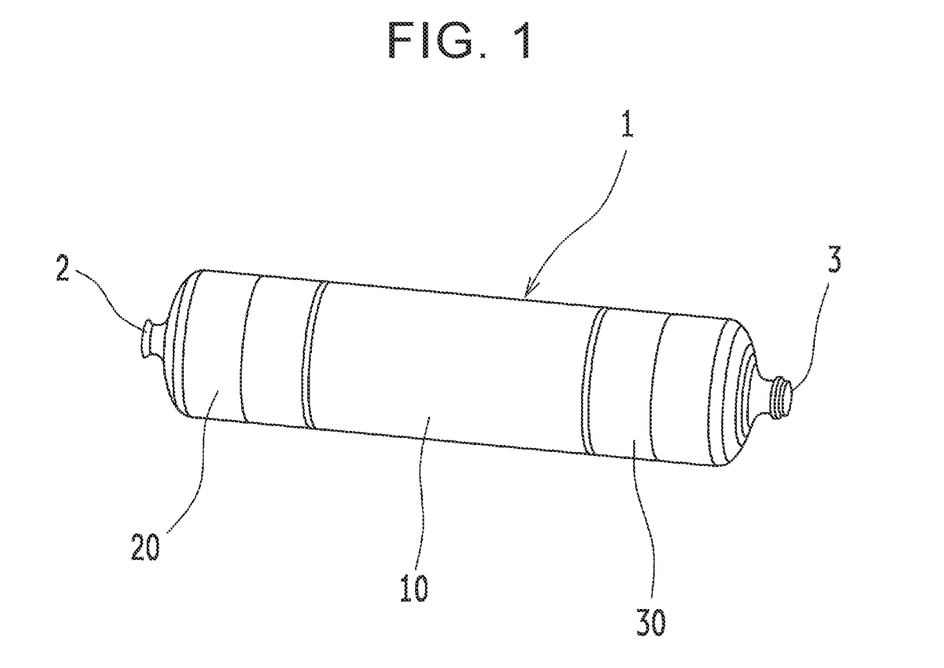
FIG. 1 is a perspective view schematically illustrating a liner according to Embodiment 1 of the present disclosure.

FIG. 1 is a perspective view schematically illustrating a liner 1 according to the present embodiment. The liner 1 constitutes an inner shell of a hydrogen tank (not shown) provided in a fuel cell vehicle, for example. The liner 1 is formed in a cylindrical shape the opposite ends of which are closed, so that high-pressure hydrogen gas used for power generation of fuel cells can be stored in the liner 1 in an airtight manner.

From the viewpoint of weight reduction, the liner 1 is made of resin and includes a pipe 10 made of resin and two domes 20, 30 made of resin as illustrated in FIG. 1. The liner 1 is formed in an airtight cylindrical shape in such a manner that one pipe 10 having a cylindrical shape is joined (welded) to the two domes 20, 30 having a bottomed tubular shape in the axial direction such that the pipe 10 is sandwiched between the domes 20, 30, and mouthpieces 2, 3 made of aluminum are assembled by press-fitting to the two domes 20, 30 placed at both ends. Then, carbon fiber (not shown) is wound around the outer periphery of the liner 1 formed as such, and hereby, a hydrogen tank having a high-strength outer shell is formed.

Figure 2:
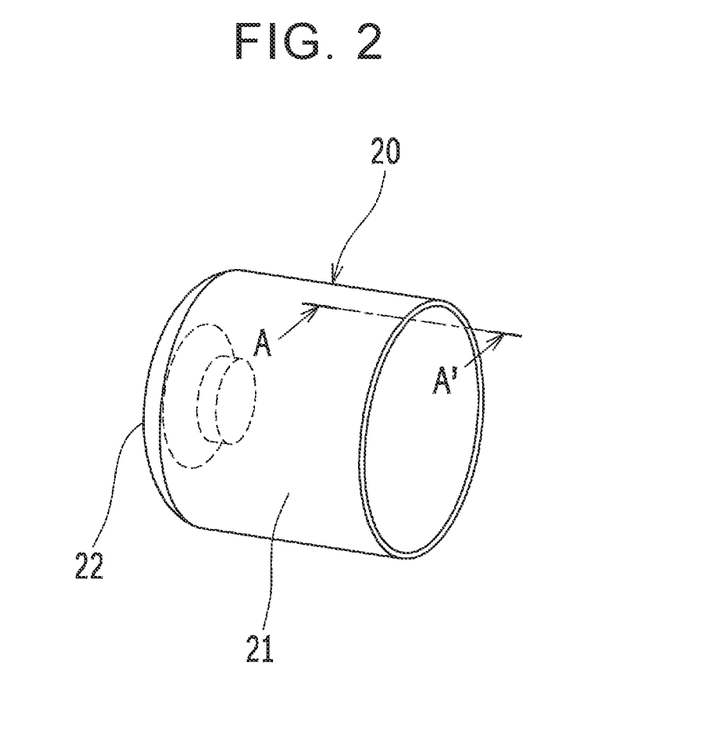
FIG. 2 is a perspective view schematically illustrating a dome.

FIG. 2 is a perspective view schematically illustrating the dome 20. The dome 20 includes a cylindrical portion 21, and a semispherical dome portion 22 provided to close one end of the cylindrical portion 21 such that the mouthpiece 2 is assembled to the semispherical dome portion 22. Thus, the dome 20 is formed in a bottomed tubular shape as described above.

Embedded Foreign Substance

In the meantime, as described above, the liner 1 serves as a container in which high-pressure hydrogen gas is filled in an airtight manner, and therefore, the liner 1 is required to have a gas barrier property to low-molecular gas. Examples of resin having such a rare characteristic called the gas barrier property include nylon and EVOH (ethylene-vinyl-alcohol copolymer). However, EVOH is hard and has poor extensibility, and its rigidity and weather resistance are also low. Accordingly, it is difficult to solely use EVOH, and EVOH is mainly used as a composite by extrusion molding and the like. In view of this, EVOH is not suitable for molding of the liner 1 that is required to have a high productivity. On this account, as a molding material for the pipe 10 and the domes 20, 30 as component parts of the liner 1, it is major to use a nylon material having a high gas barrier property. Further, in a case where the liner 1 is manufactured, it is general to mold the cylindrical pipe 10 and the bottomed tubular domes 20, 30 by injection molding in consideration of the productivity.

However, the pipe 10 and the domes 20, 30 molded by injection molding by use of the nylon material have such problems that nylon is a material that easily deteriorates and degrades due to a heat history, and it is difficult to cause the material not to remain and stay at all in an injection path. In combination of these problems, a foreign substance 40 (see FIG. 3) (hereinafter also referred to as an "embedded foreign substance 40") mainly made of a carbonized deteriorated substance and called a "black spot" may be included in the pipe 10 or the domes 20, 30. More specifically, a gap is set between a distal end of a barrel (not shown) constituting an injection path and a distal end of a screw (not shown) configured to extrude molten resin, so as to prevent a collision or bite between the barrel and the screw even in a state where the screw is advanced most. Nylon remaining and staying in such a gap is turned into a carbonized deteriorated substance due to a heat history, and the carbonized deteriorated substance peeled off is emitted into a cavity of a metal mold together with the molten resin (nylon). Hereby, the carbonized deteriorated substance is turned into the "black point." In a case where a relatively large amount of the embedded foreign substances 40 or the embedded foreign substance 40 that is relatively large is included in a product (the pipe 10 and the domes 20, 30), the mechanical strength of the liner 1 decreases as a result. In view of this, it is important to check the "amount" and "magnitude" of the embedded foreign substance 40 included in the product.

Figure 3:
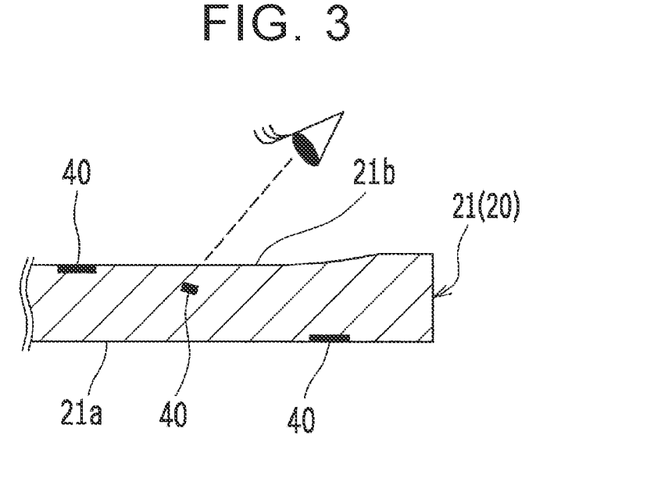
FIG. 3 is a sectional arrow view taken along a line A-A' in FIG. 2 to schematically describe an inspection of an embedded foreign substance by visual observation.

FIG. 3 is a sectional arrow view taken along a line A-A' in FIG. 2 to schematically describe an inspection of the embedded foreign substance 40 by visual observation. As illustrated in FIG. 3, the amount and magnitude of the embedded foreign substance 40 present on a surface (an outer peripheral surface 21*b*) of the dome 20 are easily checkable by visual observation. Generally, in order to prevent weatherability deterioration due to ultraviolet rays, the nylon material as the molding material for the liner 1 includes color pigment, in other words, the dome 20 is not transparent. Accordingly, as illustrated in FIG. 3, it may be said that it is difficult to check the presence or absence of the embedded foreign substance 40 present inside the dome 20, and further, it is difficult to check the magnitude of the embedded foreign substance 40 by visual observation.

Here, it is also conceivable that the embedded foreign substance 40 is detected by use of X-rays. However, from the viewpoint of an increase in cost due to introduction of an X-radiation facility or the like, safety management of X-rays (radioactive rays), and so on, the inspection by use of X-rays is unrealistic. On this account, in a case where the presence of the embedded foreign substance 40 inside the pipe 10 and the domes 20, 30 is slightly recognized by visual observation, they are all handled as defective products without checking the magnitude of the embedded foreign substance 40. This decreases the yield of the liner 1 and causes an increase in cost.

In view of this, in the present embodiment, by use of such a property that nylon that does not include color pigment allows light to pass therethrough, a dimension W0 of the embedded foreign substance 40 is calculated based on a projection image of the embedded foreign substance 40 by light emitted from a light source. The following describes details of a foreign substance inspection apparatus 50 (see FIG. 4) and a foreign substance inspection method each of which can calculate the dimension of the foreign substance 40 embedded in a tubular resin molded product (e.g., the dome 20) with high accuracy.

Foreign Substance Inspection Apparatus

Figure 4:
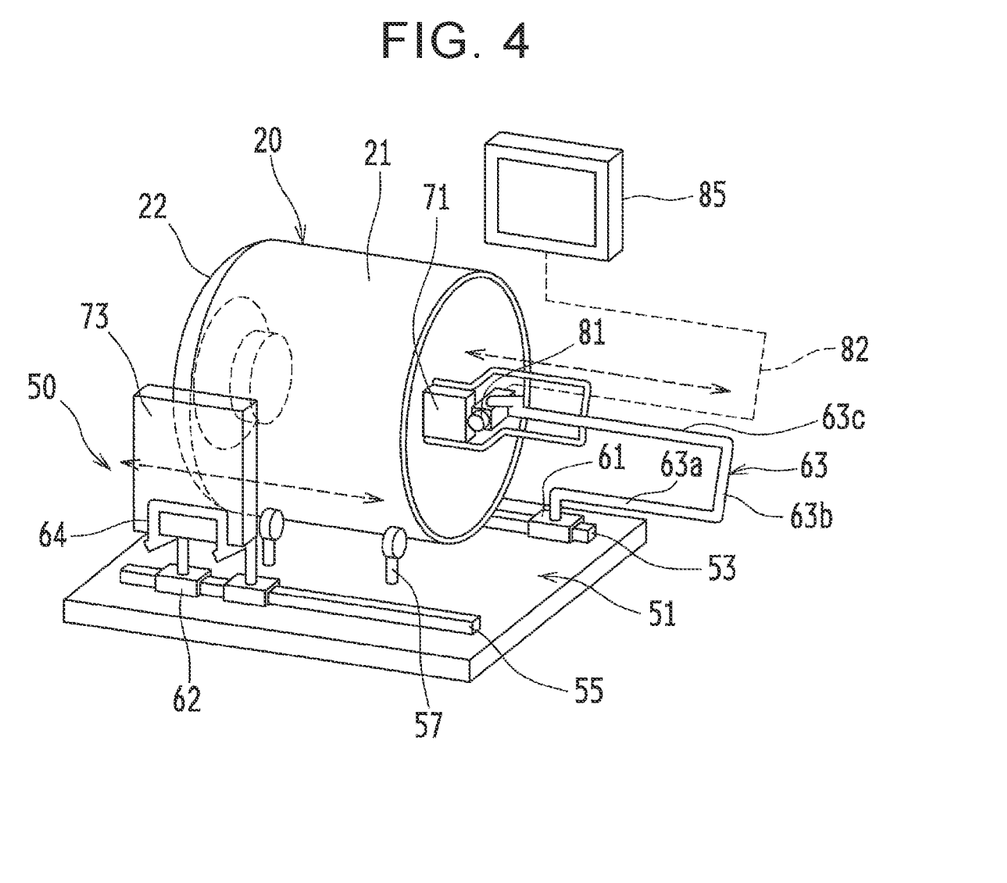
FIG. 4 is a perspective view schematically illustrating a foreign substance inspection apparatus.

FIG. 4 is a perspective view schematically illustrating the foreign substance inspection apparatus 50. As illustrated in FIG. 4, the foreign substance inspection apparatus 50 includes a base plate 51, a first slide block 61, a second slide block 62, an inner light source 71, an outer light source 73, an inner camera 81, a monitor 85, and an image processor 87 (see FIG. 7).

The base plate 51 is a rectangular disc body, and slide rails 53, 55 extending in the longitudinal direction are formed in the opposite end portions of the base plate 51 in the longitudinal right angle direction. Further, four guide rollers 57 that can support the dome 20 are provided in a central part of the base plate 51. Hereby, for example, when an inspector applies a force, in the circumferential direction, to the dome 20 placed on the guide rollers 57, the dome 20 rotates smoothly. Therefore, in terms of correspondence relations with claims, the base plate 51 provided with the four guide rollers 57 corresponds to a "support base configured to support the resin molded product such that the resin molded product is rotatable in a circumferential direction" in the present disclosure.

The first slide block 61 is attached to the slide rail 53 on the far side in FIG. 4 so as to be slidable in the longitudinal direction. The first slide block 61 is provided with an attachment arm 63 having a generally lateral U-shape. The attachment arm 63 includes: a first arm portion 63*a* extending to a first side in the longitudinal direction of the base plate 51; a second arm portion 63*b* extending to be inclined upward toward the central side of the base plate 51 from a distal end portion of the first arm portion 63*a*; and a third arm portion 63*c* extending from a distal end portion of the second arm portion 63*b* toward a second side in the longitudinal direction of the base plate 51. The attachment arm 63 is configured such that, when the inspector slides the first slide block 61 on the slide rail 53, for example, in a state where the dome 20 is placed on the guide rollers 57, the cylindrical portion 21 of the dome 20 enters between the first arm portion 63*a* and the third arm portion 63*c* so that the third arm portion 63*c* moves in the tubular axial direction inside the dome 20.

The inner light source 71 is a commercial white LED lamp, and as illustrated in FIG. 4, the inner light source 71 is attached to a distal end portion of the third arm portion 63*c*. Therefore, for example, when the inspector slides the first slide block 61 on the slide rail 53, the inner light source 71 attached to the distal end portion of the third arm portion 63*c* moves in the tubular axial direction inside the dome 20, and light is emitted from the inner light source 71 to the inner peripheral surface 21*a* of the dome 20. Note that a distance L1 from the inner light source 71 to the inner peripheral surface 21*a* of the dome 20 is set to a sufficiently short distance so that a first projection image 41 (see FIG. 5), of the embedded foreign substance 40, that is projected on the outer peripheral surface 21*b* of the dome 20 by the light from the inner light source 71 does not become blurred.

As illustrated in FIG. 4, the inner camera 81 is attached to the distal end portion of the third arm portion 63*c* together with the inner light source 71. Accordingly, for example, when the inspector slides the first slide block 61 on the slide rail 53, the inner camera 81 attached to the distal end portion of the third arm portion 63*c* moves in the tubular axial direction inside the dome 20 and captures an image of the inner peripheral surface 21*a* of the dome 20. The inner camera 81 is electrically connected to the monitor (displaying unit) 85 via a cable 82, and hereby, the image of the inner peripheral surface 21a of the dome 20, the image being captured by the inner camera 81, is displayed on a screen 85a of the monitor 85 with an appropriate reduced scale. Note that the image processor 87 will be described later.

The second slide block 62 is attached to the slide rail 55 on the near side in FIG. 4 so as to be slidable in the longitudinal direction. The second slide block 62 is provided with a generally L-shaped attachment arm 64.

Similarly to the inner light source 71, the outer light source 73 is a commercial white LED lamp, and as illustrated in FIG. 4, the outer light source 73 is attached to the attachment arm 64. Accordingly, for example, when the inspector slides the second slide block 62 on the slide rail 55, the outer light source 73 attached to the attachment arm 64 moves in the tubular axial direction outside the dome 20, and light is emitted from the outer light source 73 to the outer peripheral surface 21b of the dome 20. Note that a distance L2 from the outer light source 73 to the outer peripheral surface 21b of the dome 20 is set to a sufficiently short distance so that a second projection image 42 (see FIG. 6), of the embedded foreign substance 40, that is projected on the inner peripheral surface 21a of the dome 20 by the light from the outer light source 73 does not become blurred.

In the present embodiment, the distance L1 is set to a sufficiently short distance. Accordingly, a relatively small white LED lamp is employed as the inner light source 71 so that the inner light source 71 does not interfere with the arcuate inner peripheral surface 21a of the dome 20. In the meantime, as illustrated in FIG. 4, a relatively large white LED lamp is employed as the outer light source 73 that does not have such a restriction. However, the outer light source 73 is not limited to this, and a white LED lamp having the same size as the inner light source 71 may be employed as the outer light source 73. Note that the distance L1 from the inner light source 71 to the inner peripheral surface 21a of the dome 20 and the distance L2 from the outer light source 73 to the outer peripheral surface 21b of the dome 20 are set to the same value L. In the following description, the distance from the inner light source 71 to the inner peripheral surface 21a of the dome 20 and the distance from the outer light source 73 to the outer peripheral surface 21b of the dome 20 are both indicated by L.

Foreign Substance Inspection Method

Next will be described a foreign substance inspection method for inspecting the presence or absence of the embedded foreign substance 40 having a dimension larger than a predetermined threshold, the foreign substance inspection method being performed by use of the foreign substance inspection apparatus 50.

First, as an inspection target, the dome 20 made of nylon that does not include color pigment is prepared, and the dome 20 is placed on the guide rollers 57. As described above, generally, the nylon material as the molding material for the liner 1 includes color pigment in order to prevent weatherability deterioration due to ultraviolet rays. However, the present embodiment focuses on a point that carbon fiber is wound around the outer periphery of the liner 1 of the hydrogen tank (ultraviolet rays are prevented by carbon fiber), and the nylon material that does not include color pigment is employed as the molding material for the liner 1. Therefore, the liner 1 of the present embodiment is constituted by the pipe 10 and the domes 20, 30 that are semi-translucent such that light is passed therethrough. As such, the liner 1 that employs, as the molding material, the nylon material that does not include color pigment has such an advantage that the low-temperature tensile strength is relatively high because stress concentration due to variations in distribution of the color pigment is hard to occur.

Figure 5:
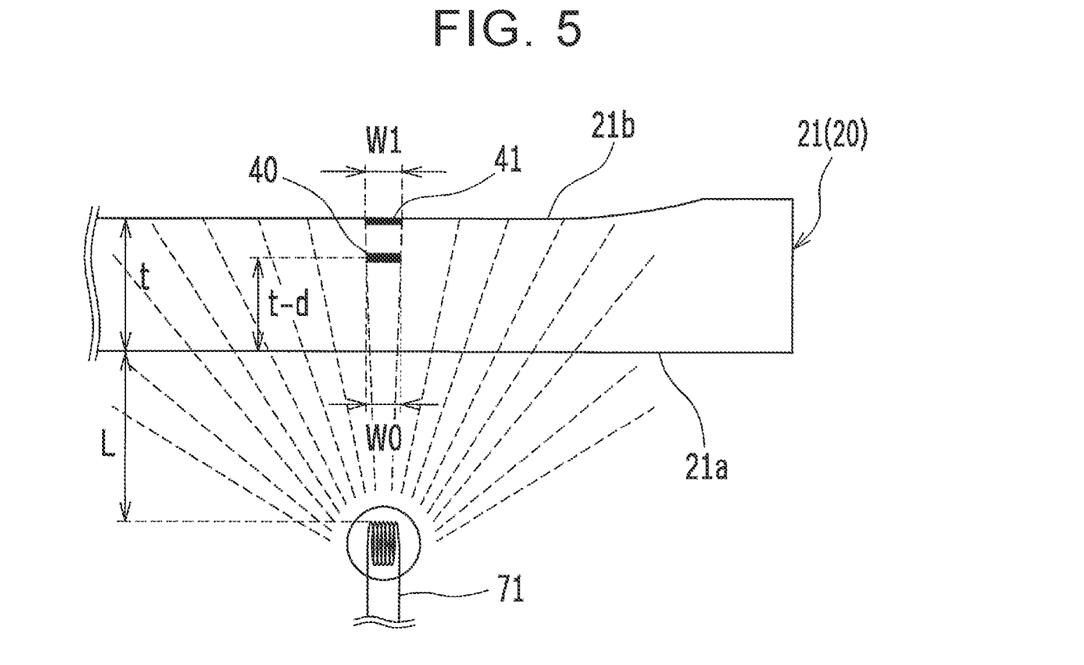
FIG. 5 is a view to schematically describe a foreign substance inspection method.
Figure 6:
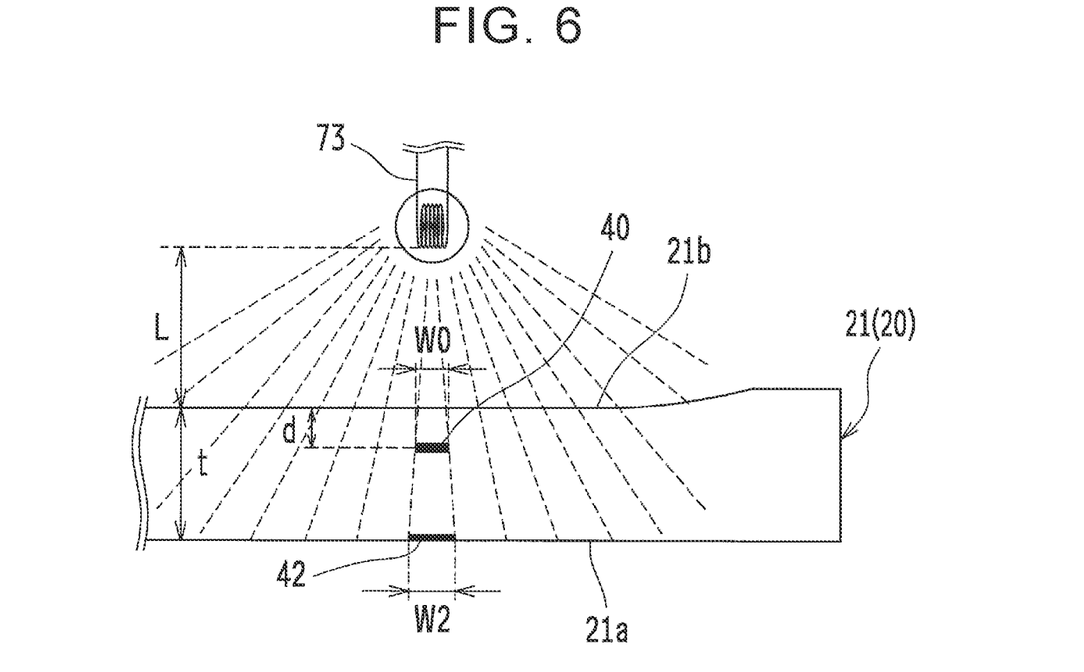
FIG. 6 is a view to schematically describe the foreign substance inspection method.

FIGS. 5 and 6 are views to schematically describe the foreign substance inspection method. The foreign substance inspection method includes a marking step, a first measurement step illustrated in FIG. 5, a second measurement step illustrated in FIG. 6, a calculation step, and a quality determination step.

First, in the marking step, a presence position of the embedded foreign substance 40 is marked on the dome 20. More specifically, while light is emitted to the inner peripheral surface 21a of the dome 20 from the inner light source 71 placed inside the dome 20 in the tubular radial direction, the first slide block 61 is roughly slid on the slide rail 53, and the dome 20 is roughly rotated on the guide rollers 57. As a result, in a case where the foreign substance 40 is embedded at a position irradiated with the light, the first projection image 41 of the embedded foreign substance 40 is projected on the outer peripheral surface 21b of the dome 20, as illustrated in FIG. 5. Then, a tape or the like is attached in the vicinity of the first projection image 41 on the outer peripheral surface 21b of the dome 20, and thus, the presence position of the embedded foreign substance 40 is marked on the outer peripheral surface 21b of the dome 20. By performing such an operation over the whole length and the whole circumference of the dome 20 through the sliding of the first slide block 61 and the rotation of the dome 20, presence positions of embedded foreign substances 40 in the dome 20 are investigated.

Subsequently, in the first measurement step, light is emitted to the inner peripheral surface 21a of the dome 20 from the inner light source 71 placed inside the dome 20 in the tubular radial direction, so that a dimension W1 of the first projection image 41, of the embedded foreign substance 40, that is projected on the outer peripheral surface 21b is measured. More specifically, light is emitted to the inner peripheral surface 21a of the dome 20 from the inner light source 71 with the tape attached in the marking step as a mark, and as illustrated in FIG. 5, the first projection image 41 of the embedded foreign substance 40 is projected on the outer peripheral surface 21b of the dome 20. As such, since the first projection image 41 projected on the outer peripheral surface 21b of the dome 20 is checkable by the inspector by visual observation, the dimension W1 of the first projection image 41 is measured by use of a gauge or the like.

Subsequently, in the second measurement step, light is emitted to the outer peripheral surface 21b of the dome 20 from the outer light source 73 placed outside the dome 20 in the tubular radial direction, and a dimension W2 of the second projection image 42, of the embedded foreign substance 40, that is projected on the inner peripheral surface 21a is measured. More specifically, light is emitted to the outer peripheral surface 21b of the dome 20 from the outer light source 73 with the tape attached in the marking step as a mark, and as illustrated in FIG. 6, the second projection image 42 of the embedded foreign substance 40 is projected on the inner peripheral surface 21a of the dome 20. As such, since it is difficult for the inspector to check, by visual observation, the second projection image 42 projected on the inner peripheral surface 21a of the dome 20, an image of the second projection image 42 is captured by the inner camera 81, and the captured image of the second projection image 42 is displayed on the screen 85a of the monitor 85.

Figure 7:
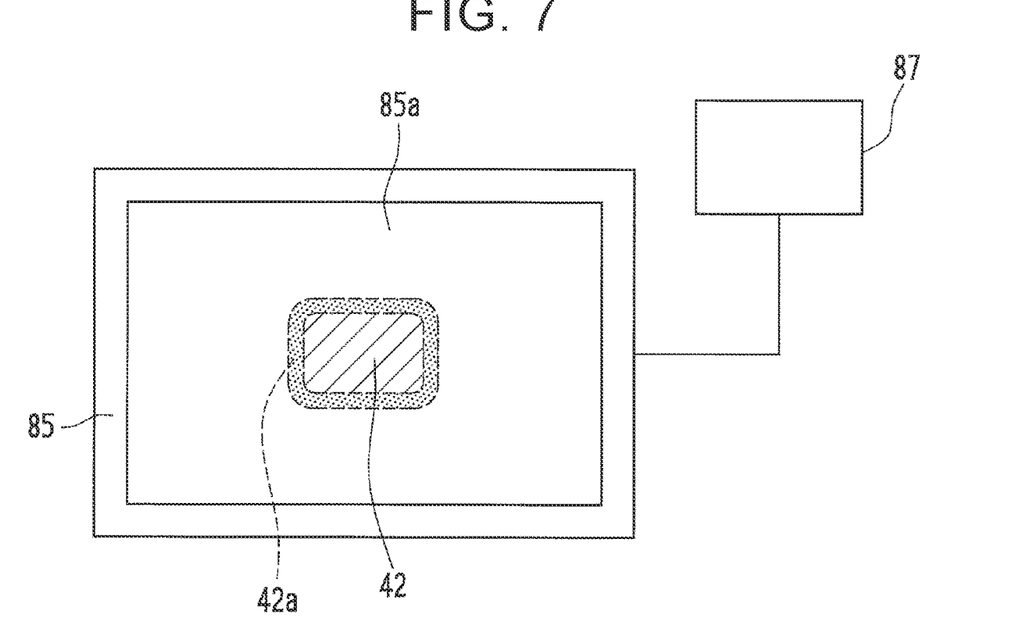
FIG. 7 is a view schematically illustrating a monitor and an image processor.

FIG. 7 is a view schematically illustrating the monitor 85 and the image processor 87. As illustrated in FIG. 7, the image of the second projection image 42 is displayed on the screen 85a of the monitor 85. However, a border 42a of the second projection image 42 may be blurred as indicated by dot hatching in FIG. 7, and therefore, determination by the inspector is required. More specifically, the inspector specifies the border 42a of the second projection image 42 displayed on the screen 85a by use of a pointer (not shown) or the like on the screen, so that the image processor 87 measures the dimension of the second projection image 42. The image processor 87 is a device that can measure the dimension of the embedded foreign substance 40 based on image data or the like, and the image processor 87 can be achieved, for example, such that an image processing program, a determination program, and so on are incorporated into a general-purpose personal computer. Note that, in terms of correspondence relations with claims, the image processor 87 corresponds to a "measuring unit configured to measure a dimension of a projection image of the embedded foreign substance when an inspector specifies, on the screen, a border of the projection image, of the embedded foreign substance, that is displayed on the displaying unit" in the present disclosure.

By performing such an operation on all the embedded foreign substances 40 marked in the marking step, the dimensions W1, W2 of the first and second projection images 41, 42 of the embedded foreign substances 40 can be obtained. Note that, in the present embodiment, the dimensions of the projection images are measured in order of the first measurement step and the second measurement step. However, the first measurement step and the second measurement step may be performed in reverse order to the above.

In the calculation step, the dimension W0 of the embedded foreign substance 40 is calculated based on a proportional relationship between the dimension W1 of the first projection image 41 (or the dimension W2 of the second projection image 42) to the distance from the inner light source 71 (or the outer light source 73) to the first projection image 41 (or the second projection image 42) and the dimension W0 of the embedded foreign substance 40 to the distance from the inner light source 71 (or the outer light source 73) to the embedded foreign substance 40. The calculation step includes a first calculation step and a second calculation step.

In the first calculation step, an embedment depth d of the embedded foreign substance 40 is calculated based on the proportional relationship between the dimension W1 of the first projection image 41 to the distance from the inner light source 71 to the first projection image 41 (the outer peripheral surface 21b) and the dimension W0 of the embedded foreign substance 40 to the distance from the inner light source 71 to the embedded foreign substance 40, and the proportional relationship between the dimension W2 of the second projection image 42 to the distance from the outer light source 73 to the second projection image 42 (the inner peripheral surface 21a) and the dimension W0 of the embedded foreign substance 40 to the distance from the outer light source 73 to the embedded foreign substance 40. Then, by use of the embedment depth d thus calculated, a distance L0 from the outer light source 73 to the embedded foreign substance 40 is calculated.

More specifically, when the thickness of the cylindrical portion 21 of the dome 20 is taken as t, and the embedment depth of the embedded foreign substance 40 from the outer peripheral surface 21b is taken as d, a proportional relationship as expressed by Equation (1) is established between the dimension W1 of the first projection image 41 and the dimension W0 of the embedded foreign substance 40, as seen from FIG. 5.

$$W0:W1=L+t-d:L+t \qquad \text{Equation (1)}$$

When Equation (1) is rearranged, Equation (2) is established.

$$W0=(L+t-d)/(L+t) \times W1 \qquad \text{Equation (2)}$$

Further, as seen from FIG. 6, a proportional relationship as expressed by Equation (3) is established between the dimension W2 of the second projection image 42 and the dimension W0 of the embedded foreign substance 40.

$$W0:W2=L+d:L+t \qquad \text{Equation (3)}$$

When Equation (3) is rearranged, Equation (4) is established.

$$W0=(L+d)/(L+t) \times W2 \qquad \text{Equation (4)}$$

Here, the distance L, the thickness t, the dimension W1, and the dimension W2 are known, and only two values, i.e., the dimension W0 of the embedded foreign substance 40 and the embedment depth d of the embedded foreign substance 40 are unknown. Accordingly, the dimension W0 and the embedment depth d of the embedded foreign substance 40 can be calculated from two equations, i.e., Equation (2) and Equation (4).

First, the dimension W0 of the embedded foreign substance 40 is eliminated from Equation (2) and Equation (4), and an obtained equation is rearranged in terms of the embedment depth d of the embedded foreign substance 40. Hereby, Equation (5) is obtained.

$$d=[W1 \times t+(W1-W2) \times L]/(W1+W2) \qquad \text{Equation (5)}$$

Hereby, the distance L0 (=L+d) from the outer light source 73 to the embedded foreign substance 40 is calculated.

In the subsequent second calculation step, the dimension W0 of the embedded foreign substance 40 is calculated based on the proportional relationship between the dimension W2 of the second projection image 42 to the distance from the outer light source 73 to the second projection image 42 and the dimension W0 of the embedded foreign substance 40 to the distance L0.

More specifically, by substituting the distance L0 into Equation (4), the dimension W0 of the embedded foreign substance 40 is calculated by Equation (6).

$$W0=L0/(L+t) \times W2 \qquad \text{Equation (6)}$$

Subsequently, in the quality determination step, it is determined whether or not the dimension W0 of the embedded foreign substance 40, calculated in the calculation step, is a predetermined threshold or less. More specifically, when the dimension W0 of the embedded foreign substance 40 exceeds the threshold (e.g., 0.6 mm), the dome 20 in which the embedded foreign substance 40 is embedded is handled as a defective product. In the meantime, when the dimension W0 of the embedded foreign substance 40 is the threshold or less, the dome 20 in which the embedded foreign substance 40 is embedded is handled as a non-defective product. Even in a case where the dimension W0 of the embedded foreign substance 40 is the threshold or less, when the number of the embedded foreign substances 40 exceeds a predetermined number (e.g., 5 per 100 $mm^2$), the dome 20 including the embedded foreign substances 40 the number of which exceeds the predetermined number is handled as a defective product.

Thus, with the present embodiment, the dimension W0 of the embedded foreign substance 40 can be calculated with high accuracy by a safe and simple technique to emit light from the inner and outer light sources 71, 73 in the tubular radial direction to the dome 20 made of nylon that does not include color pigment.

Embodiment 2

The present embodiment is different from Embodiment 1 in that an image of the first projection image 41 projected on the outer peripheral surface 21b of the dome 20 by the inner light source 71 is also captured by a camera. The following mainly describes points different from Embodiment 1.

The dimension of the first projection image 41 projected on the outer peripheral surface 21b of the dome 20 by light from the inner light source 71 can be measured by the inspector by visual observation regardless of the size of the diameter of the liner 1. On the other hand, it might be difficult for the inspector to measure, by visual observation, the dimension of the second projection image 42 projected on the inner peripheral surface 21a of the dome 20 by light from the outer light source 73 depending on the size of the diameter of the liner 1. On this account, in Embodiment 1, an image of the second projection image 42 projected on the inner peripheral surface 21a of the dome 20 is captured by the inner camera 81, so that the dimension W2 of the second projection image 42 is measured based on the image thus captured.

However, in a case where the dimension of a first projection image is directly measured by visual inspection, and the dimension of a second projection image is measured via a captured image, a slight measurement error might be caused between them.

In view of this, in the present embodiment, images of the first and second projection images 41, 42 are both captured by respective cameras, and the dimensions W1, W2 of the first and second projection images 41, 42 are measured based on the images thus captured.

Figure 8:
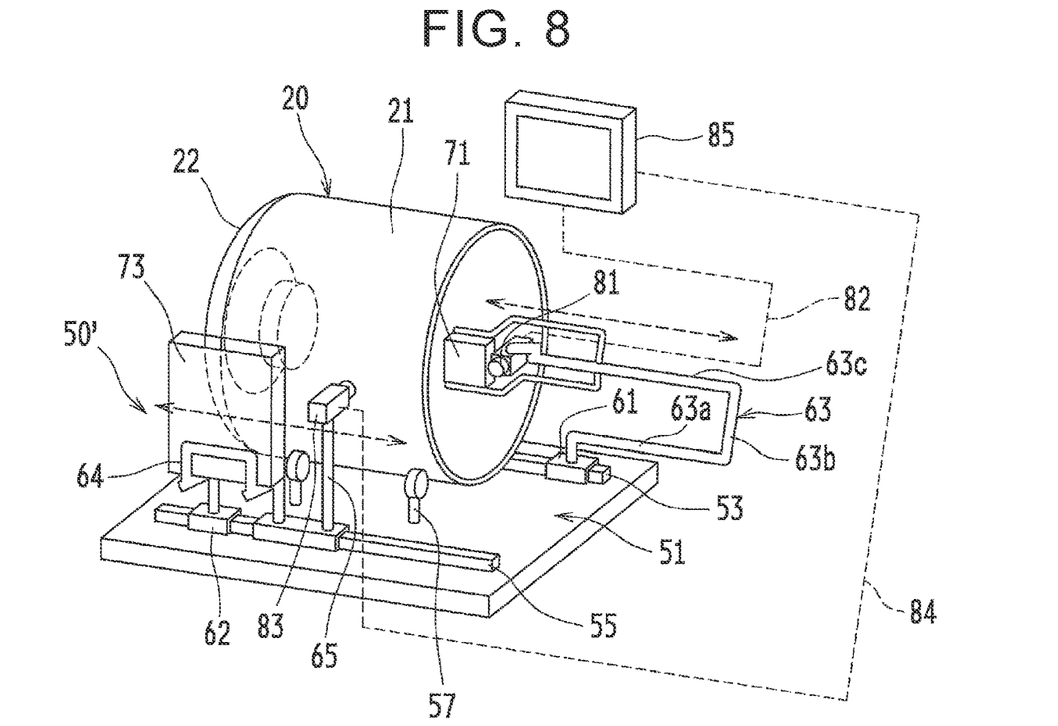
FIG. 8 is a perspective view schematically illustrating a foreign substance inspection apparatus according to Embodiment 2 of the present disclosure.

FIG. 8 is a perspective view schematically illustrating a foreign substance inspection apparatus 50' according to the present embodiment. As illustrated in FIG. 8, the second slide block 62 of the foreign substance inspection apparatus 50' is provided with a bar-shaped attachment arm 65 extending upward, in addition to the generally L-shaped attachment arm 64. An outer camera 83 is attached to a distal end portion of the attachment arm 65. Accordingly, for example, when the inspector slides the second slide block 62 on the slide rail 55, the outer camera 83 attached to the distal end portion of the attachment arm 65 moves outside the dome 20 in the tubular axial direction and captures an image of the outer peripheral surface 21b of the dome 20. The outer camera 83 is electrically connected to the monitor 85 via a cable 84, and hereby, the image, of the outer peripheral surface 21b of the dome 20, that is captured by the outer camera 83 is displayed on the screen 85a of the monitor 85 with an appropriate reduced scale.

Thus, in the first measurement step, light is emitted to the inner peripheral surface 21a of the dome 20 from the inner light source 71 with the tape attached in the marking step as a mark, and the first projection image 41 of the embedded foreign substance 40 is projected on the outer peripheral surface 21b of the dome 20. Hereby, an image of the first projection image 41 projected on the outer peripheral surface 21b of the dome 20 is captured by the outer camera 83, and the captured image of the first projection image 41 is displayed on the screen 85a of the monitor 85. When the inspector specifies a border of the first projection image 41 displayed on the screen 85a by use of a pointer or the like on the screen, the dimension W1 of the first projection image 41 is measured by the image processor 87.

In the present embodiment, the dimensions W1, W2 of the first and second projection images 41, 42, of the embedded foreign substance 40, that are projected on the inner peripheral surface 21a and the outer peripheral surface 21b, respectively, are measured by the same measurement technique, so that a measurement error can be restrained.

Other Embodiments

The present disclosure is not limited to the above embodiments and can be carried out in other various forms without departing from the spirit or main feature of the present disclosure.

In the above embodiments, the dome 20 is an inspection target. However, the present disclosure is not limited to this. The pipe 10 and the dome 30 may be inspection targets.

Further, in the above embodiments, the present disclosure is applied to a member (the dome 20) constituting the liner 1. However, the present disclosure may be applied to a member other than members constituting the liner 1, provided that the member is a tubular member made of resin which does not include color pigment and which has a property that allows light to pass through the resin.

Further, in the above embodiments, the dome 20 is rotated manually, and the inner and outer light sources 71, 73 and so on are moved manually. However, the present disclosure is not limited to this. For example, the guide roller 57 and the first and second slide blocks 61, 62 may be configured to be electrically driven, and the rotation of the dome 20 and the movement of the inner and outer light sources 71, 73, and the like may be controlled by a computer.

Further, in the above embodiments, the distance L1 from the inner light source 71 to the inner peripheral surface 21a of the dome 20 and the distance L2 from the outer light source 73 to the outer peripheral surface 21b of the dome 20 are set to the same distance L. However, the present disclosure is not limited to this. The distance L1 and the distance L2 may be set to different distances.

Further, in the above embodiments, at least the inner camera 81 is used. However, in a case where the diameter of the liner 1 is sufficiently large, the present disclosure is not limited to this, and the dimension W2 of the second projection image 42 may be also measured by the inspector by visual observation.

Thus, the above embodiments are just examples in every respect and must not be interpreted restrictively. Further, modifications and alterations belonging to an equivalent range of Claims are all included in the present disclosure.

With the present disclosure, it is possible to calculate, with high accuracy, the dimension of a foreign substance embedded in a tubular resin molded product by a safe and simple technique. Accordingly, the present disclosure is extremely useful when the present disclosure is applied to a foreign substance inspection method and a foreign substance inspection apparatus each for inspecting the presence or absence of a foreign substance embedded in a tubular resin molded product and having a dimension larger than a predetermined threshold.

What is claimed is:
1. A foreign substance inspection method for inspecting presence or absence of a foreign substance embedded in a tubular resin molded product and having a dimension larger than a predetermined threshold, the foreign substance inspection method comprising:

preparing, as the resin molded product, a resin molded product made of nylon that does not include color pigment;

a first measurement step of emitting light to a first peripheral surface of the resin molded product from a first light source and measuring a dimension of a first projection image, of an embedded foreign substance, that is projected on a second peripheral surface, the first light source being placed on either one of inside and outside of the resin molded product in a tubular radial direction;

a second measurement step of emitting light to the second peripheral surface of the resin molded product from a second light source and measuring a dimension of a second projection image, of the embedded foreign substance, that is projected on the first peripheral surface, the second light source being placed on the other one of the inside and the outside of the resin molded product in the tubular radial direction; and a calculation step of calculating a dimension of the embedded foreign substance based on a proportional relationship between a dimension of each of the projection images projected by the light sources to a distance from a corresponding one of the light sources to the each of the projection images and a dimension of the embedded foreign substance to a distance from the corresponding one of the light sources to the embedded foreign substance.

2. The foreign substance inspection method according to claim 1, wherein the calculation step includes:

a first calculation step of calculating a distance from either one of the first and second light sources to the embedded foreign substance by use of an embedment depth of the embedded foreign substance, the embedment depth being calculated based on a proportional relationship between the dimension of the first projection image to a distance from the first light source to the first projection image and the dimension of the embedded foreign substance to a distance from the first light source to the embedded foreign substance, and a proportional relationship between the dimension of the second projection image to a distance from the second light source to the second projection image and the dimension of the embedded foreign substance to a distance from the second light source to the embedded foreign substance; and a second calculation step of calculating the dimension of the embedded foreign substance based on a proportional relationship between the dimension of a projection image projected by the one of the first and second light sources to the distance from the one of the first and second light sources to the projection image and the dimension of the embedded foreign substance to the distance from the one of the first and second light sources to the embedded foreign substance.

3. The foreign substance inspection method according to claim 1, wherein, in the first and second measurement steps, images of the first and second projection images are captured by respective cameras, and respective dimensions of the first and second projection images are measured based on the images thus captured.

4. A foreign substance inspection apparatus used for the foreign substance inspection method according to claim 1, the foreign substance inspection apparatus comprising:

an inner light source placed inside the resin molded product in the tubular radial direction such that the inner light source is movable in a tubular axial direction;

an outer light source placed outside the resin molded product in the tubular radial direction such that the outer light source is movable in the tubular axial direction;

a support base configured to support the resin molded product such that the resin molded product is rotatable in a circumferential direction;

a camera placed at least inside the resin molded product in the tubular radial direction such that the camera is movable in the tubular axial direction, the camera being configured to take an image of an inner peripheral surface of the resin molded product;

a displaying unit configured to display the image captured by the camera on a screen; and a measuring unit configured to measure a dimension of a projection image of the embedded foreign substance when an inspector specifies, on the screen, a border of the projection image, of the embedded foreign substance, that is displayed on the displaying unit.

5. The foreign substance inspection apparatus according to claim 4, further comprising a camera placed outside the resin molded product in the tubular radial direction such that the camera is movable in the tubular axial direction, the camera being configured to capture an image of an outer peripheral surface of the resin molded product.

* * * * *